(12) United States Patent
Muramatsu et al.

(10) Patent No.: US 9,902,661 B2
(45) Date of Patent: Feb. 27, 2018

(54) METHOD FOR PRODUCING HYDROCARBON (71) Applicant: TOYOTA JIDOSHA KABUSHIKI KAISHA, Toyota-shi, Aichi-ken (JP)

(72) Inventors: Masayoshi Muramatsu, Aichi (JP); Chikara Ohto, Aichi (JP)

(73) Assignee: TOYOTA JIDOSHA KABUSHIKI KAISHA, Toyota-shi, Aichi (JP)

( * ) Notice: Subject to any disclaimer, the term of this patent is extended or adjusted under 35 U.S.C. 154(b) by 0 days.

(21) Appl. No.: 15/159,922

(22) Filed: May 20, 2016

(65) Prior Publication Data

US 2016/0340269 A1 Nov. 24, 2016

(30) Foreign Application Priority Data

May 22, 2015 (JP) .................................. 2015-104366

(51) Int. Cl.
*C07C 1/207* (2006.01)
*B01J 23/08* (2006.01)
*B01J 23/22* (2006.01)

(52) U.S. Cl.
CPC ...... *C07C 1/2076* (2013.01); *C07C 2527/053* (2013.01); *C07C 2527/055* (2013.01); *C07C 2527/06* (2013.01); *C07C 2527/128* (2013.01); *C07C 2527/132* (2013.01); *C07C 2527/133* (2013.01); *C07C 2527/135* (2013.01); *C07C 2527/138* (2013.01)

(58) Field of Classification Search
None
See application file for complete search history.

(56) References Cited

U.S. PATENT DOCUMENTS

| 4,263,443 | A | * | 4/1981 | White | C07C 1/2076 549/429 |
| 4,277,375 | A | * | 7/1981 | Decker | B01J 23/28 502/241 |
| 4,517,400 | A | * | 5/1985 | Pesa | C07C 1/2076 585/638 |
| 7,138,544 | B2 | | 11/2006 | Springer et al. | |
| 7,799,945 | B2 | | 9/2010 | Springer | |
| 8,492,584 | B2 | | 7/2013 | Teles et al. | |
| 2012/0016159 | A1 | * | 1/2012 | Liang | B01J 23/002 562/532 |

FOREIGN PATENT DOCUMENTS

ES 2371718 A1 1/2012
JP 5248603 A 4/1977

OTHER PUBLICATIONS

Schirmer et al., "Microbial Biosynthesis of Alkanes", Science, Jul. 30, 2010, pp. 559-562, vol. 329, <www.sciencemag.org>.

(Continued)

*Primary Examiner* — Philip Y Louie
(74) *Attorney, Agent, or Firm* — Sughrue Mion, PLLC (57) ABSTRACT A method for producing a linear hydrocarbon, including reacting a linear aliphatic aldehyde in the presence of at least one metal ion selected from the group consisting of a vanadium ion, a manganese ion, an iron ion, a cobalt ion, an iridium ion, a copper ion, and a thallium ion.

10 Claims, 4 Drawing Sheets (56) References Cited

OTHER PUBLICATIONS

Zhang et al., "Conversion of fatty aldehydes into alk (a/e)nes by in vitro reconstituted cyanobacterial aldehyde-deformylating oxygenase with the cognate electron transfer system", Biotechnology for Biofuels, 2013, pp. 1-10, vol. 6:86, BioMed Central Ltd.

Roa et al., Decarbonylation of Aliphatic Aldehydes by a $Tp^{Me2}Ir(III)$ Metallacyclopentadiene, Organometallics, Jan. 9, 2012, pp. 716-721, vol. 31, ACS Publications.

Iwai et al., "The iridium-catalyzed decarbonylation of aldehydes under mild conditions", Chem. Commun., Oct. 29, 2008, pp. 6215-6217, The Royal Society of Chemistry, <www.rsc.org/chemcomm>.

Modak et al., "A general and efficient aldehyde decarbonylation reaction by using a palladium catalyst", Chem Comm, 2012, pp. 4253-4255, vol. 48, The Royal Society of Chemistry.

Kogan, V., et al., "Polyoxometalates as Reduction Catalysts: Deoxygenation and Hydrogenation of Carbonyl Compounds", Angew. Chem. Int. Ed., 1999, vol. 38, No. 22, pp. 3331-3334.

Das, D., et al., "Oxygen-independent decarbonylation of aldehydes by cyanobacterial aldehyde decarbonylase: a new reaction of di-iron enzymes", Angew. Chem. Int. Ed. in English, 2011, vol. 50, No. 31, pp. 7148-7152 (p. 1-14), Supporting Information.

* cited by examiner

METHOD FOR PRODUCING HYDROCARBON

CROSS REFERENCE TO RELATED APPLICATIONS

The disclosure of Japanese Patent Application No. JP 2015-104366 filed on May 22, 2015 is incorporated herein by reference in its entirety.

TECHNICAL FIELD

Aspects of the present disclosure relate to a method for producing a linear hydrocarbon from a linear aliphatic aldehyde.

BACKGROUND

Recently, the development of biofuel has been underway in order to cope with the issue of oil depletion and reduce carbon dioxide emissions. One example of a biofuel is biodiesel fuel. Biodiesel fuel containing a hydrocarbon in a certain percentage is expected to be used as an alternative of light oil.

A known example of a method for producing a hydrocarbon is a method comprising reducing an aldehyde using an enzyme or a metal catalyst. For example, Non-Patent Document 1 (Schirmer, Andreas et al., Microbial Biosynthesis of Alkanes, Science, 2010, 329(5991), 559-562) discloses a method for producing a hydrocarbon from an aldehyde using an enzyme, comprising converting acyl-ACP, which is an intermediate of fatty acid synthesis, into an aldehyde with the use of acyl-ACP reductase (AAR) and then converting the aldehyde into a hydrocarbon and CO with the use of aldehyde decarbonylase (AD). In addition, Non-Patent Document 2 (Jingjing Zhang et al., Conversion of fatty aldehydes into alk (a/e)nes by in vitro reconstituted cyanobacterial aldehyde-defortnylating oxygenase with the cognate electron transfer system, Biotech, Biofuels, 2013, 6(86). 1-10) discloses conversion of an aldehyde into a hydrocarbon and formic acid. However, AD has low enzyme activity and is inactivated by $H_2O_2$, which is generated by NADPH necessary for reaction. In a method using AD, it is difficult to avoid enzyme deactivation caused by $H_2O_2$ generated during reaction, which results in significant reduction in enzyme reaction efficiency. For the above reasons, it is difficult to convert an aldehyde into a hydrocarbon with high efficiency through a method using an enzyme.

In addition, as an example of a method for producing a hydrocarbon from an aldehyde using a metal catalyst, Non-Patent Document 3 (Arian E. Roa et al., Decarbonylation of Aliphatic Aldehydes by a $Tp^{Me2}Ir$ (III) Metallacyclopentadiene, Organometallics, 2012, 31, 716-721) discloses a decarbonylation reaction of aliphatic aldehydes by a $Tp^{Me2}Ir$ (III) metallacyclopentadiene. Further, Non-Patent Document 4 (Tomohiro Iwai et al., The iridium-catalyzed decarbonylation of aldehydes under mild condition. Chem. Commun., 2008, 6215-6217) discloses a decarbonylation reaction of aldehydes by using an iridium catalyst. Furthermore, Non-Patent Document 5 (Atanu Modak et al., A general and efficient aldehyde decarbonylation reaction by using a palladium catalyst, Chem. Commun., 2012, 48, 4253-4255) discloses a decarbonylation reaction of aldehydes by using a palladium catalyst. However, in the cases of the conventional methods using metal catalysts, a reaction is carried out using an organic solvent at a relatively high temperature. Therefore, it is desirable to safely carry out the reaction under mild conditions.

SUMMARY

As described above, in the conventional methods for producing a hydrocarbon from an aldehyde using an enzyme, the hydrocarbon sometimes cannot be efficiently obtained due to deactivation of the enzyme. In addition, it is desirable to safely carry out a reaction under mild conditions in the conventional methods for producing a hydrocarbon from an aldehyde using a metal catalyst. Therefore, an object of the present disclosure is to provide a method for producing a hydrocarbon by which a reaction can be safely carried out under mild conditions to efficiently produce such hydrocarbon.

As a result of intensive studies to achieve the above object, it was found that it is possible to safely carry out a reaction under mild conditions by reacting a linear aliphatic aldehyde in the presence of a specific metal ion so as to efficiently produce a linear hydrocarbon. This has led to the present disclosure described herein.

Specifically, aspects of the present disclosure are summarized as follows.

(1) A method for producing a linear hydrocarbon that includes reacting a linear aliphatic aldehyde in the presence of at least one metal ion selected from the group consisting of a vanadium ion, a manganese ion, an iron ion, a cobalt ion, an iridium ion, a copper ion, and a thallium ion.

(2) The method according to (1), wherein the linear aliphatic aldehyde is a linear aliphatic aldehyde having 8 to 18 carbon atoms.

(3) The method according to (1) or (2), wherein the reaction is carried out in a solvent containing water.

According to aspects of the present disclosure, a method for producing a hydrocarbon by which a reaction can be safely carried out under mild conditions to efficiently produce such hydrocarbon can be provided.

DETAILED DESCRIPTION

Hereinafter, embodiments of the present disclosure are described.

An embodiment of the present disclosure is a method for producing a linear hydrocarbon, including reacting a linear aliphatic aldehyde in the presence of a specific metal ion. According to aspects of this embodiment, a linear hydrocarbon is produced as a result of a decarbonylation reaction of a linear aliphatic aldehyde. That is, a linear hydrocarbon having one less carbon atom than its original linear aliphatic aldehyde is generated.

From the standpoint of the amount of the hydrocarbon produced, a linear aliphatic aldehyde used is preferably a linear aliphatic aldehyde having 8 to 18 carbon atoms and more preferably a linear aliphatic aldehyde having 10 to 16 carbon atoms.

The linear aliphatic aldehyde may be a linear saturated aliphatic aldehyde having an alkyl moiety consisting of a saturated bond or a linear unsaturated aliphatic aldehyde having an alkyl moiety containing an unsaturated bond.

The linear saturated aliphatic aldehyde is preferably a linear saturated aliphatic aldehyde having 8 to 18 carbon atoms and more preferably a linear saturated aliphatic aldehyde having 10 to 16 carbon atoms. Examples of such preferable linear saturated aliphatic aldehyde include octanal, nonanal, decanal, undecanal, dodecanal, tridecanal, tetradecanal, pentadecanal, hexadecanal, heptadecanal, and octadecanal.

The linear unsaturated aliphatic aldehyde is preferably a linear unsaturated aliphatic aldehyde having 8 to 18 carbon atoms and more preferably a linear unsaturated aliphatic aldehyde having 10 to 16 carbon atoms. In addition, the linear unsaturated aliphatic aldehyde is preferably a linear unsaturated aliphatic aldehyde having at least one carbon-carbon double bond in its molecule and more preferably a linear unsaturated aliphatic aldehyde having one carbon-carbon double bond in its molecule. Examples of such preferable linear unsaturated aliphatic aldehyde include 4-tetradecenal, 8-tetradecenal, 3-hexadecenal, 11-hexadecenal, and 2-nonenal.

A metal ion used in the present disclosure is at least one selected from the group consisting of a vanadium ion, a manganese ion, an iron ion, a cobalt ion, an iridium ion, a copper ion, and a thallium ion. From the standpoint of the amount of the hydrocarbon produced, a metal ion used in the present disclosure is preferably a vanadium ion, a manganese ion, an iron ion, or a cobalt ion, more preferably a vanadium ion or a cobalt ion, and particularly preferably a vanadium ion.

The valence of the above metal ion is not particularly limited. For example, when the metal ion is a vanadium ion, either a vanadium (II) ion or a vanadium (IV) ion can be used. When the metal ion is an iron ion, either an iron (II) ion or an iron (III) ion can be used. Also, the metal ion may be a combination of at least two metal ions having different valences.

A metal ion used in the present disclosure is preferably a vanadium (II) ion, a vanadium (IV) ion, a manganese (VII) ion, an iron (II) ion, an iron (III) ion, a cobalt (II) ion, an iridium (IV) ion, a copper (II) ion, or a thallium (III) ion. From the standpoint of the amount of the hydrocarbon produced, it is more preferably a vanadium (II) ion, a vanadium (IV) ion, a manganese (VII) ion, an iron (II) ion, an iron (III) ion, or a cobalt (II) ion and particularly preferably a vanadium (II) ion, a vanadium (IV) ion, or a cobalt (II) ion.

It is preferable to add a metal compound to a reaction system, thereby allowing its metal ion to be present in the reaction system. Examples of a metal compound include inorganic acid salts, organic acid salts, and halides of metals. Inorganic acid salts and halides of metals are preferable. A metal compound may be in the form of a hydrate.

Examples of a vanadium compound from which a vanadium ion is generated include, but are not particularly limited to, vanadium trichloride oxide, vanadium sulfate oxide, vanadium octanoate, vanadium oxalate oxide, vanadium naphthenate, vanadium chloride, vanadium bromide, vanadium oxydichloride, vanadium oxytrichloride, sodium orthovanadate, cesium orthovanadate, rubidium orthovanadate, ammonium metavanadate, lithium metavanadate, sodium metavanadate, potassium metavanadate, and cesium metavanadate. Of these, vanadium (IV) sulfate oxide ($VOSO_4$) and vanadium (II) chloride ($VCl_2$) are preferable.

Examples of a manganese compound from which a manganese ion is generated include, but are not particularly limited to, manganese sulfate, ammonium manganese sulfate, manganese nitrate, a monobasic salt of manganese phosphate, manganese acetate, manganese butyrate, manganese 2-ethylhexanoate, manganese stearate, manganese benzoate, manganese chloride, manganese bromide, and potassium permanganate. Of these, potassium permanganate ($KMnO_4$) is preferable.

Examples of an iron compound from which an iron ion is generated include, but are not particularly limited to, iron nitrate, iron chloride, iron bromide, iron sulfate, iron phosphate, iron hydroxide, iron oxide, iron hydrogen carbonate, and iron carbonate. Of these, iron (II) sulfate (FeSO4) and iron (III) chloride (FeCl3) are preferable.

Examples of a cobalt compound from which a cobalt ion is generated include, but are not particularly limited to, cobalt hydroxide, cobalt acetate, cobalt nitrate, cobalt sulfate, cobalt oxalate, and cobalt chloride. Of these, cobalt (II) chloride (CoCl2) is preferable.

Examples of an iridium compound from which an iridium ion is generated include, but are not particularly limited to, iridium chloride, chloroiridic acid, diammonium hexachloroiridate, triammonium hexachloroiridate, dipotassium hexachloroiridate, and tripotassium hexachloroiridate. Of these, iridium (IV) chloride ($IrCl_4$) and diammonium hexachloroiridate (($NH_4)_2IrCl_6$) are preferable.

Examples of a copper compound from which a copper ion is generated include, but are not particularly limited to, copper chloride, copper bromide, copper nitrate, copper phosphate, copper sulfate, copper acetate, copper carbonate, and copper oxalate. Of these, copper sulfate ($CuSO_4$) is preferable.

Examples of a thallium compound from which a thallium ion is generated include, but are not particularly limited to, thallium sulfate, thallium acetate, thallium nitrate, thallium iodide, thallium chloride, and thallium hydroxide. Of these, thallium (III) chloride (TlCl3) is preferable.

Examples of a preferable combination of a linear aliphatic aldehyde and a metal ion include, but are not particularly limited to, a combination of a linear aliphatic aldehyde having 9 to 17 carbon atoms and a vanadium ion, a combination of a linear aliphatic aldehyde having 11 to 13 carbon atoms and a manganese ion, a combination of a linear aliphatic aldehyde having 9 to 16 carbon atoms and an iron ion, a combination of a linear aliphatic aldehyde having 9 to 11 carbon atoms and a cobalt ion, a combination of a linear aliphatic aldehyde having 11 carbon atoms and an iridium ion, a combination of a linear aliphatic aldehyde having 11 carbon atoms and a copper ion, and a combination of a linear aliphatic aldehyde having 11 carbon atoms and a thallium ion.

It is preferable to carry out a reaction in a solvent containing water in order to ionize a metal compound to its corresponding metal ion. A solvent is preferably water (e.g., distilled water, ion-exchange water, or ultrapure water) in consideration of safety and the amount of the hydrocarbon produced; however, a solvent may contain an organic solvent as long as a metal compound can be ionized to its corresponding metal ion. Examples of an organic solvent that can be used include, but are not particularly limited to: alcohol solvents such as methanol, ethanol, isopropyl alcohol, and t-butanol; ketone solvents such as acetone, methyl ethyl ketone, and methyl isobutyl ketone; ester solvents such as methyl acetate, ethyl acetate, and butyl acetate; polar aprotic solvents such as N,N-dimethylformamide, dimethyl sulfoxide, sulfolane, and N-methylpyrrolidone; glycol ether solvents such as diethylene glycol monomethyl ether and propylene glycol monomethylether acetate; glycol solvents such as ethylene glycol and propylene glycol; ether solvents such as diethyl ether, tetrahydrofuran, and dioxane; aliphatic hydrocarbon solvents such as petroleum ether, hexane, and hexene; aromatic hydrocarbon solvents such as toluene, xylene, and benzene; organic chlorine solvents such as chloroform, carbon tetrachloride, and trichloroethylene; and terpene solvents such as limonene, squalene, and lycopene. A solvent is selected depending on the solubility of a linear aliphatic aldehyde used as a material. It is preferable for a linear aliphatic aldehyde to be dissolved in a solvent in the reaction of the present disclosure; however, a linear aliphatic aldehyde may at least be suspended or dispersed. The amount of an organic solvent in a solvent accounts for generally 0.1% to 200% by weight, preferably 1% to 100% by weight, and more preferably 10% to 50% by weight of the total amount of the solvent.

The concentration of a metal ion in a solvent is determined depending on a linear aliphatic aldehyde and the metal ion to be used. The concentration of a metal ion in a solvent is not particularly limited; however, it is generally 0.1 ppm to 2000 ppm and preferably 50 ppm to 500 ppm. When the concentration of a metal ion in a solvent falls within the above range, the amount of the hydrocarbon produced increases. For example, the concentration of a metal ion in a solvent is preferably 100 ppm to 500 ppm for a vanadium ion, 200 ppm to 1000 ppm for a manganese ion, 200 ppm to 2000 ppm for an iron ion, and 500 ppm to 1000 ppm for a cobalt ion.

The concentration of a linear aliphatic aldehyde in a solvent is generally 0.1 mM to 20 mM, but it is not limited thereto.

The ratio of a linear aliphatic aldehyde to a metal ion in a solvent is generally 1:2 to 1:1000.

The reaction temperature is generally 10° C. to 90° C. From the standpoint of the amount of the hydrocarbon produced, it is preferably 20° C. to 40° C. Note that when an iron ion or a copper ion is used at a concentration of 1000 ppm or more, the temperature is preferably 90° C. or more.

The reaction pressure is generally ordinary pressure. The term "ordinary pressure" refers herein to atmospheric pressure around the standard atmospheric pressure (1013 hPa) that is obtained without intended pressurization or depressurization. Such atmospheric pressure is generally 800 to 1050 hPa and usually 1000 to 1030 hPa.

The reaction is preferably carried out at ordinary pressure.

The reaction time is changed depending on type, concentration, reaction temperature, and other conditions regarding the linear aliphatic aldehyde and the metal ion to be used; however, it is generally 5 minutes to 48 hours.

The pH of the reaction system can be determined depending on the metallic ion to be used and its concentration, and it is generally pH 8 or less. When a vanadium ion, a manganese ion, an iron ion, and a cobalt ion are used, the pH of the reaction system is preferably pH 5 or less in view of the amount of the hydrocarbon produced.

The reaction can be carried out by, for example, mixing a linear aliphatic aldehyde and a metal compound in a solvent to react. A linear aliphatic aldehyde and a metal compound can be mixed by, for example, mixing a linear aliphatic aldehyde that has been dissolved, suspended, or dispersed in the above solvent or organic solvent with an aqueous solution of a metal compound. The full amount of a linear aliphatic aldehyde may be added at once to a metal compound or it may be divided into two or more portions to be added to a metal compound.

It is possible to purify a generated linear hydrocarbon by, for example, extracting it with the use of an organic solvent at the end of a reaction and subjecting the resulting extract to ordinary posttreatment such as distillation of the organic solvent. Examples of an organic solvent that can be used for extraction include, but are not limited to, the aforementioned alcohol solvents, ketone solvents, ester solvents, polar aprotic solvents, glycol ether solvents, glycol solvents, ether solvents, aliphatic hydrocarbon solvents, aromatic hydrocarbon solvents, organic chlorine solvents, and terpene solvents. If a solvent used in a reaction contains an organic solvent, it is possible to omit the extraction of a generated linear hydrocarbon with the use of an organic solvent.

EXAMPLES

The present disclosure is more specifically described with reference to the Examples below. However, the scope of the present disclosure is not limited to the Examples.

Example 1

Vanadium sulfate oxide ($VOSO_4$), cobalt chloride hexahydrate ($CoCl_2 \cdot 6H_2O$), ferrous sulfate heptahydrate ($FeSO_4 \cdot 7H_2O$), copper sulfate pentahydrate ($CuSO_4 \cdot 5H_2O$), and ferric chloride ($FeCl_3$) were used as metal compounds. In addition, chromium chloride hexahydrate ($CrCl_3 \cdot 6H_2O$), rubidium chloride (RbCl), zirconium oxide ($ZrO_2$), and molybdenum sulfate dihydrate ($MoSO_4 \cdot 2H_2O$) were used as metal compounds in a Comparative Example. A reaction was also carried out without the addition of a metal compound for a control.

Each of the above metal compounds was added to 200 μL of a sodium phosphate buffer (100 mM, pH 7.0) containing tetradecanal (at a final concentration of 10 mM; obtained from Tokyo Chemical Industry Co., Ltd.) to result in a final concentration of 50 ppm. Reaction was carried out in a closed Eppendorf tube at 37° C. for 14 hours. Next, 200 μL of ethyl acetate was added to and sufficiently mixed with the reaction solution, followed by centrifugation (4° C., 20000 g, 5 minutes). Then, 150 μL of the resulting ethyl acetate layer was transferred to a 250 μL vial bottle with the microvolume insert and subjected to GC/MS analysis using a GC/MS system (6890/5973) of Agilent Technologies. Upon GC/MS analysis, a 1 mM tetradecanal in N,N-dimethylformamide solution, a 4.11 mM (1 mL/mL) tridecane in ethanol solution, and a 4.39 mM (1 mg/mL) meristic acid in ethanol solution were used as standards.

<Analysis Conditions>
GC/MS Temperature
Inlet temperature: 260° C.
MS zone temperature
MS Quad: 150° C.
MS Source: 230° C.
Scan Parameter
Low Mass: 50
High Mass: 550
Threshold: 150

Injection Parameter
Mode: Automatic injection
Sample volume: 5 μL
Number of times of washing: Washing twice with ethyl acetate and twice with chloroform
Split ratio: 1:20
Carrier gas: Helium 1.0 mL/minute
Solvent delay: 2.6 minutes
Oven temperature increase condition: Retention for 1 minute at 60° C., temperature increase at 50° C./minute to 320° C., and retention for 5 minutes
Post-time: 0
Column: Agilent Technologies HP-5MS (φ0.25 mm×30 m; film thickness: 0.25 mm).

Figure 1:
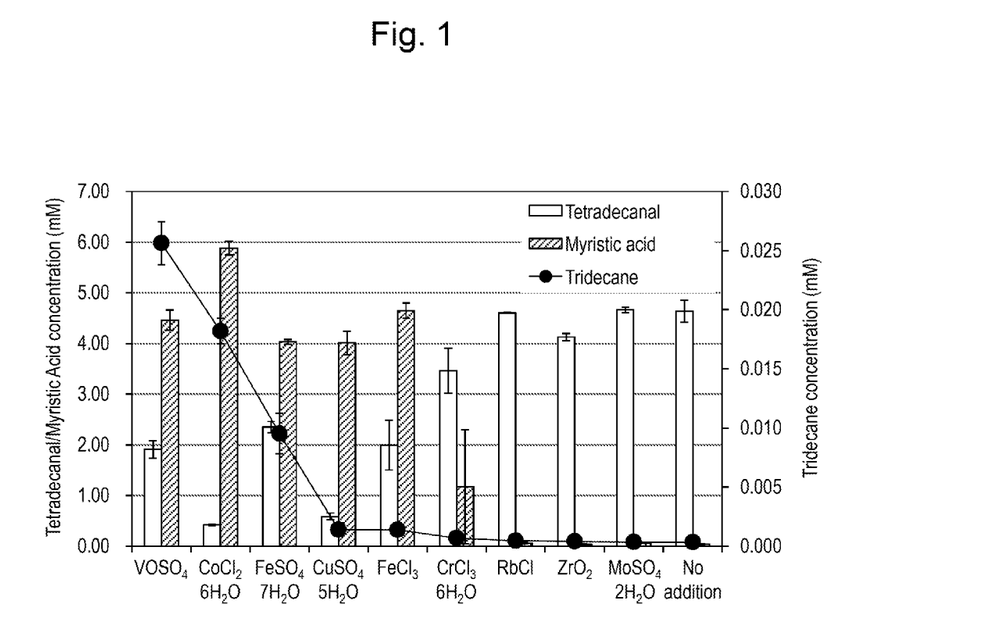
FIG. 1 shows the amounts of tridecane and myristic acid produced with the use of different metal compounds and the residual amount of tetradec anal in Example 1.

FIG. 1 shows the results. FIG. 1 shows the amounts of tridecane and myristic acid produced with the use of different metal compounds (50 ppm each) and the residual amount of tetradecanal. In FIG. 1, the error bar represents a sample standard deviation (n=2).

FIG. 1 shows that when vanadium sulfate oxide, cobalt chloride, ferrous sulfate, copper sulfate, ferric chloride, and chromium chloride were each used, tetradecanal was reacted to generate myristic acid and tridecane. However, when chromium chloride was used, a small amount of tetradecanal was reacted and thus a large amount of residual tetradecanal used as a starting material was left. When vanadium sulfate oxide, cobalt chloride, and ferrous sulfate were each used, a significantly large amount of tridecane was produced. When rubidium chloride, zirconium oxide, and molybdenum sulfate were each used in the Comparative Example, the amount of residual tetradecanal used as a starting material was substantially equivalent to that in the control case in which no metal compound had been added. This means that substantially no tetradecanal was reacted. The tetradecanal concentration decreased by half (4.64 mM) in the case in which no metal compound had been added, which was probably due to the obtained extraction efficiency (about 80%) and adsorption to the Eppendorf tube. In addition, ferrous sulfate and ferric chloride have different iron ion valences. In view of this, the amount of tridecane produced with the use of ferrous sulfate, which is a divalent iron compound, was greater than that for ferric chloride, which is a trivalent iron compound.

Example 2

Tetradecanal was used as a linear aliphatic aldehyde to react in the presence of different metal ions.

Firstly, in order to precisely determine the amount of tridecane obtained as a reaction product and the amount of tetradecanal used as a starting material, internal standards were examined for analysis. As a result, 2-octanol was found to be an appropriate internal standard substance. The standard solutions of different concentrations of tridecane and tetradecanal were each mixed with 2-octanol used as an internal standard solution at a ratio of 1:3, followed by GC/MS analysis. The obtained relative peak areas were calculated. The correlation coefficients obtained for tridecane and tetradecanal were as high as 0.9999 and 0.9893, respectively.

Secondly, different metal compounds were weighed and dissolved or uniformly dispersed in water to prepare aqueous solutions of the metal compounds (1% by weight). 200 μL of sodium phosphate buffers (100 mM, pH 7.0) containing tetradecanal (at a final concentration of 10 mM; obtained from Tokyo Chemical Industry Co., Ltd.) and a final concentration of 0.1 ppm, 10 ppm, or 50 ppm of each metal compound were prepared by addition of the obtained aqueous solutions, followed by reaction at 30° C. for 3 hours and then GC/MS analysis. Table 1 lists the results.

TABLE 1

Amounts of tridecane (μM) generated by reaction of tetradecanal in the presence of different metal ions

| Metal Compound | Metal compound concentration | | |
|---|---|---|---|
| | 50 ppm | 10 ppm | 0.1 ppm |
| $VCl_2$ | 174.7 | 8.1 | 0.0 |
| $CoCl_2 \cdot 6H_2O$ | 123.1 | 1.7 | |
| $VOSO_4$ | 62.3 | 19.4 | |
| $FeSO_4 \cdot 7H_2O$ | 12.7 | 3.0 | |
| $KMnO_4$ | 11.2 | 7.1 | 0.1 |
| $CuSO_4 \cdot 5H_2O$ | 5.5 | 7.3 | |
| $FeCl_3 \cdot 6H_2O$ | 4.5 | 0.8 | |
| $(NH_4)_2IrCl_6$ | 2.0 | 0.3 | 0.1 |
| $TlCl_3$ | 1.9 | 0.3 | 0.3 |
| $EuCl_2$ | 0.6 | 0.6 | 0.5 |
| $IrCl_4$ | 0.6 | 0.5 | 0.3 |
| $Na_3VO_4$ | 0.6 | 0.0 | 0.0 |
| $NH_4Cl$ | 0.5 | 0.2 | 0.3 |
| $MoCl_5$ | 0.5 | 0.2 | 0.2 |
| $TbCl_3$ | 0.4 | 0.4 | 0.4 |
| $NiCl_2$ | 0.4 | 0.1 | 0.0 |
| $SmCl_3$ | 0.3 | 0.5 | 0.5 |
| $CrCl_2$ | 0.3 | 0.5 | 0.5 |
| $PrCl_3$ | 0.3 | 0.4 | 0.6 |
| $K_3[Fe(CN)_6]$ | 0.3 | 0.1 | 0.3 |
| $ScCl_3$ | 0.3 | 0.0 | 0.0 |
| $LiTaO_3$ | 0.3 | 0.0 | 0.0 |
| $Na_2MoO_4 \cdot 2H_2O$ | 0.3 | | |
| $YCl_3$ | 0.2 | 0.4 | 0.6 |
| $Na_3(PO_4 \cdot 12MoO_3) \cdot nH_2O$ | 0.2 | 0.2 | 0.2 |
| $MgCl_2 \cdot 6H_2O$ | 0.2 | 0.2 | 0.0 |
| $InCl_3$ | 0.2 | 0.1 | 0.3 |
| $Na_2WO_4 \cdot 2H_2O$ | 0.2 | 0.1 | 0.2 |
| $K_4[Fe(CN)_6]$ | 0.2 | 0.1 | 0.2 |
| $MoO_3$ | 0.2 | 0.1 | 0.2 |
| $H_3BO_3$ | 0.2 | 0.1 | 0.1 |
| $RhCl_3 \cdot 3H_2O$ | 0.2 | 0.1 | 0.1 |
| $NaVO_3$ | 0.2 | 0.0 | 0.0 |
| $CeCl_3$ | 0.2 | 0.0 | 0.0 |
| $NaCl$ | 0.2 | 0.0 | 0.0 |
| $SnCl_2$ | 0.1 | 0.3 | 0.3 |
| $SrCl_2 \cdot 6H_2O$ | 0.1 | 0.3 | 0.0 |
| $AlCl_3$ | 0.1 | 0.2 | 0.4 |
| $B_2O_3$ | 0.1 | 0.1 | 0.2 |
| $CaCl_2$ | 0.1 | 0.0 | 0.1 |
| $ErCl_3$ | 0.1 | 0.0 | 0.1 |
| $KCl$ | 0.1 | 0.0 | 0.1 |
| $CrO_3$ | 0.1 | 0.0 | 0.0 |
| $Na_2B_4O_7$ | 0.0 | 0.2 | 0.1 |
| $GdCl_3 \cdot 6H_2O$ | 0.0 | 0.2 | 0.0 |
| $CsCl$ | 0.0 | 0.2 | 0.0 |
| $H_2PtCl_6$ | 0.0 | 0.1 | 0.3 |
| $RbCl$ | 0.0 | 0.1 | 0.2 |
| $LuCl_3$ | 0.0 | 0.1 | 0.2 |
| $RuO_4$ | 0.0 | 0.1 | 0.1 |
| $[Co(NH_4)_6]Cl_3$ | 0.0 | 0.1 | 0.1 |
| $SbCl_3$ | 0.0 | 0.1 | 0.1 |
| $PdCl_2$ | 0.0 | 0.1 | 0.1 |
| $TmCl_3 \cdot 6H_2O$ | 0.0 | 0.1 | 0.1 |
| $PtCl_4$ | 0.0 | 0.1 | 0.0 |
| $YbCl_3$ | 0.0 | 0.1 | 0.0 |
| $MnSO_4 \cdot 5H_2O$ | 0.0 | 0.0 | 0.2 |
| $HoCl_3 \cdot 6H_2O$ | 0.0 | 0.0 | 0.1 |
| $ZnCl_2$ | 0.0 | 0.0 | 0.1 |
| $EuCl_3 \cdot 6H_2O$ | 0.0 | 0.0 | 0.1 |
| $AgNO_3$ | 0.0 | 0.0 | 0.1 |
| $OsCl_3$ | 0.0 | 0.0 | 0.1 |
| $V_2O_5$ | 0.0 | 0.0 | 0.1 |
| $K_2CrO_4$ | 0.0 | 0.0 | 0.1 |
| $HfCl_4$ | 0.0 | 0.0 | 0.1 |
| $LiCl$ | 0.0 | 0.0 | 0.0 |
| $Zr(SO_4)_2$ | 0.0 | 0.0 | 0.0 |

9

TABLE 1-continued

Amounts of tridecane (μM) generated by reaction of
tetradecanal in the presence of different metal ions

| Metal Compound | Metal compound concentration | | |
|---|---|---|---|
| | 50 ppm | 10 ppm | 0.1 ppm |
| $CdCl_2 \cdot 2.5H_2O$ | 0.0 | 0.0 | 0.0 |
| $NdCl_3$ | 0.0 | 0.0 | 0.0 |
| KI | 0.0 | 0.0 | 0.0 |
| $DyCl_3 \cdot 6H_2O$ | 0.0 | 0.0 | 0.0 |
| $Na_2ZrO_3$ | 0.0 | 0.0 | 0.0 |
| $TeCl_4$ | 0.0 | 0.0 | 0.0 |
| NaF | 0.0 | 0.0 | 0.0 |
| KBr | 0.0 | 0.0 | 0.0 |
| $LaCl_3 \cdot 7H_2O$ | 0.0 | 0.0 | 0.0 |
| $BaCl_2$ | 0.0 | 0.0 | 0.0 |
| $CrCl_3 \cdot 6H_2O$ | 0.0 | | |
| $ZrO_2$ | 0.0 | | |

Table 1 shows that large amounts of tridecane were generated when vanadium chloride ($VCl_2$), cobalt chloride hexahydrate ($CoCl_2.6H_2O$), vanadium sulfate oxide ($VOSO_4$), ferrous sulfate heptahydrate ($FeSO_4.7H_2O$), potassium permanganate ($KMnO_4$), copper sulfate pentahydrate ($CuSO_4.5H_2O$), ferric chloride hexahydrate ($FeCl_3.6H_2O$), diammonium hexachloroiridate (($NH_4)_2$ $IrCl_6$), and thallium chloride ($TlCl_3$) were used as metal compounds.

Example 3

Figure 2:
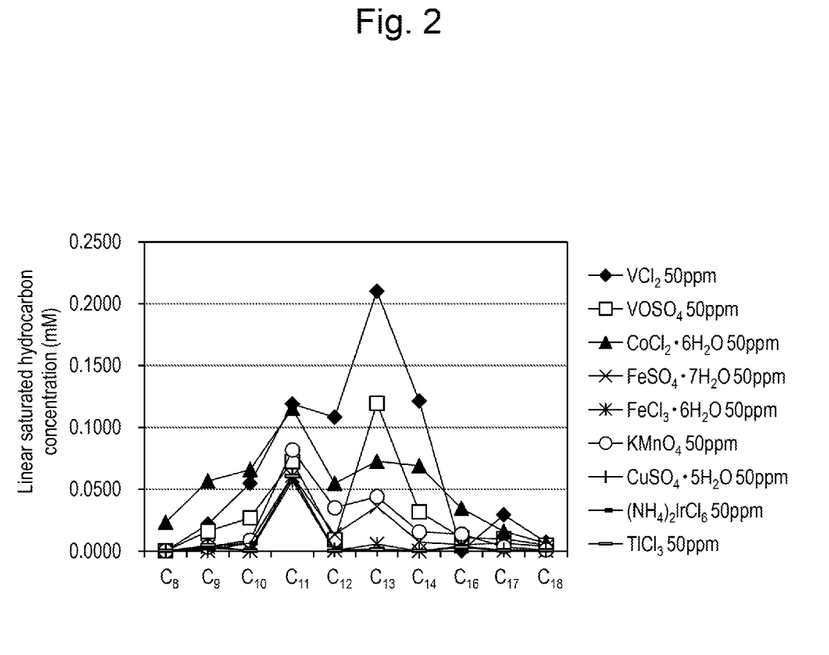
FIG. 2 shows the amounts of linear saturated hydrocarbons produced with the use of different linear saturated aliphatic aldehydes at a final metal compound concentration of 50 ppm in Example 3.
Figure 3:
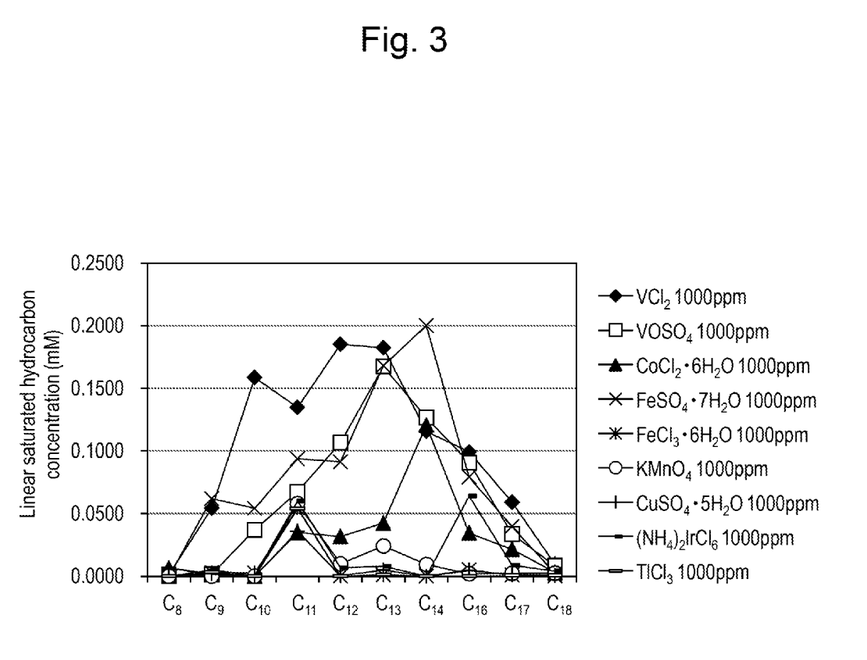
FIG. 3 shows the amounts of linear saturated hydrocarbons produced with the use of different linear saturated aliphatic aldehydes at a final metal compound concentration of 1000 ppm in Example 3.

Different types of linear aliphatic aldehydes were allowed to react in the presence of different types of metal ions. Different linear saturated aliphatic aldehydes having 8 to 18 carbon atoms were used as linear aliphatic aldehydes. metal compounds used herein were vanadium chloride ($VCl_2$), cobalt chloride hexahydrate ($CoCl_2.6H_2O$), vanadium sulfate oxide ($VOSO_4$), ferrous sulfate heptahydrate ($FeSO_4.7H_2O$), potassium permanganate ($KMnO_4$), copper sulfate pentahydrate ($CuSO_4.5H_2O$), ferric chloride hexahydrate ($FeCl_3.6H_2O$), diammonium hexachloroiridate (($NH_4)_2$ $IrCl_6$), and thallium chloride ($TlCl_3$). Aqueous solutions of different metal compound were separately added to the above linear saturated aliphatic aldehydes (1 mM, not fully dissolved in some cases) to result in a final concentration of 50 ppm or 1000 ppm, followed by reaction at 30° C. for 3 hours. Each resultant was extracted with ethyl acetate and subjected to GC/MS analysis. FIGS. 2 and 3 show the results. FIG. 2 shows the amounts of linear saturated hydrocarbons produced from different linear saturated aliphatic aldehydes at a final metal compound concentration of 50 ppm. FIG. 3 shows the amounts of linear saturated hydrocarbons produced from different linear saturated aliphatic aldehydes at a final metal compound concentration of 1000 ppm.

FIGS. 2 and 3 show that the corresponding linear saturated hydrocarbons were produced from the above linear saturated aliphatic aldehydes having 8 to 18 carbon atoms at a final metal compound concentration of either 50 ppm or 1000 ppm.

Next, 2-nonenal and 11-hexadecenal, which are linear unsaturated aliphatic aldehydes, were each used as a linear aliphatic aldehyde to carry out a reaction in the same manner. The corresponding linear unsaturated hydrocarbons were obtained from both compounds.

10

Example 4

Vanadium chloride ($VCl_2$) was used as a metal compound, tetradecanal was used as a linear aliphatic aldehyde, and water or a liquid mixture of water and ethyl acetate was used as a solvent.

(1) System Containing Water as a Solvent

Sodium phosphate buffer (50 mM, pH 7.0) (20 μL), tetradecanal dissolved in DMF (100 mM; obtained from Tokyo Chemical Industry Co., Ltd.) (20 μL), and ion-exchange water (140 μL) were introduced into a 1.5 mL Eppendorf tube. A 500 ppm aqueous solution of vanadium chloride ($VCl_2$) (20 μL) was added to the obtained solution, followed by mixing with the vortex mixer. The mixed solution was incubated on a heat block at 30° C. for 10 minutes and then transferred to an incubator, followed by heating at 30° C. for 2 hours and 50 minutes. Thereafter, 200 μL of ethyl acetate was added to the reaction solution and sufficiently mixed therewith for 5 minutes with a shaker, followed by centrifugation (4° C. 12000 rpm, 1 minute). Then, 150 μL of the resulting ethyl acetate layer was transferred to a vial bottle with the microvolume insert comprising 50 μL of an internal standard solution (0.4% 2-octanol/2-propanol), mixed therewith with the vortex mixer, and subjected to GC/MS analysis using a GC/MS system (6890/5973) of Agilent Technologies.

For comparison, reaction was carried out in the above manner except that 20 μL of the 500 ppm aqueous solution of vanadium chloride ($VCl_2$) was replaced with 20 μL of ion-exchange water.

(2) System Containing a Liquid Mixture of Water and Ethyl Acetate as a Solvent

Sodium phosphate buffer (50 mM, pH 7.0) (20 μL), tetradecanal dissolved in DMF (100 mM, obtained from Tokyo Chemical Industry Co., Ltd.) (20 μL), and ion-exchange water (140 μL) were transferred into a 1.5 mL Eppendorf tube. Ethyl acetate (200 μL) and a 500 ppm aqueous solution of vanadium chloride ($VCl_2$) (20 μL) were added to the obtained solution, followed by mixing with a vortex mixer. The mixed solution was incubated on a heat block at 30° C. for 10 minutes and then transferred to an incubator, followed by heating at 30° C. for 2 hours and 50 minutes. The reaction solution was sufficiently mixed for 5 minutes with a shaker, followed by centrifugation (4° C., 12000 rpm, 1 minute). Then, 150 μL of the resulting ethyl acetate layer was transferred to a vial bottle with an insert comprising 50 μL of an internal standard solution (0.4% 2-octanol/2-propanol), mixed therewith with a vortex mixer, and subjected to GC/MS analysis using a GC/MS system (6890/5973) of Agilent Technologies.

For comparison, reaction was carried out in the above manner except that 20 μL of the 500 ppm aqueous solution of vanadium chloride ($VCl_2$) was replaced with 20 μL of ion-exchange water.

Figure 4:
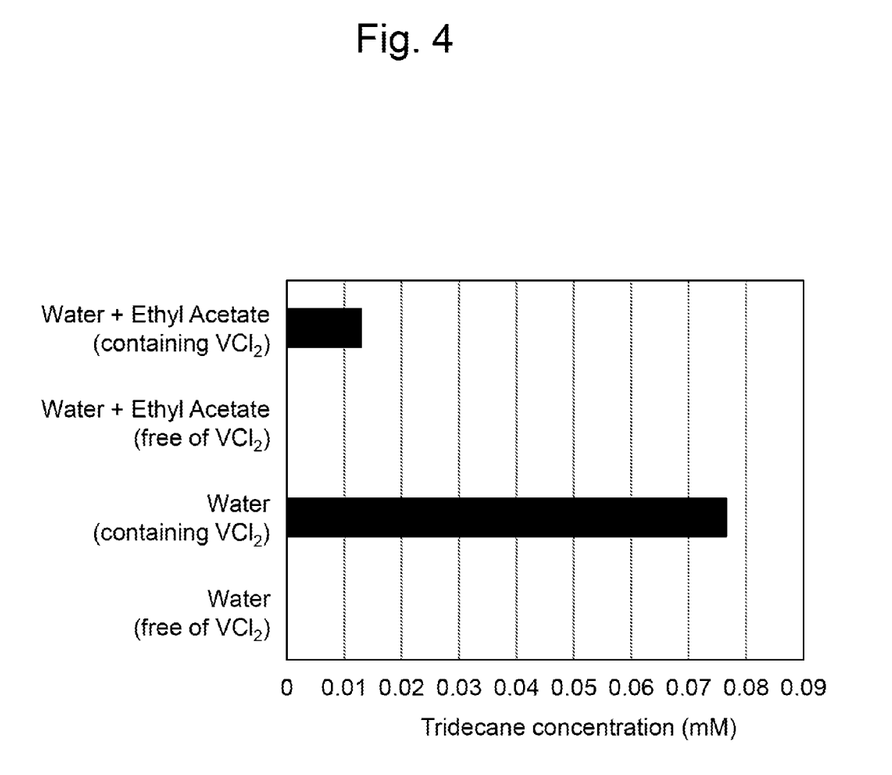
FIG. 4 shows the tridecane concentration with the use of water or a liquid mixture of water and ethyl acetate as a solvent in Example 4.

FIG. 4 shows the results. As is understood from FIG. 4, when vanadium chloride was added, tridecane was generated with the use of either water (water (containing $VCl_2$) in FIG. 4) or a liquid mixture of water and ethyl acetate (water+ethyl acetate (containing $VCl_2$) in FIG. 4) as a solvent. Meanwhile, when vanadium chloride was not added, tridecane was not generated with the use of either water (water (free of $VCl_2$) in FIG. 4) or a liquid mixture of water and ethyl acetate (water+ethyl acetate (free of $VCl_2$) in FIG. 4) as a solvent.

The method of the present disclosure enables efficient production of a linear hydrocarbon from a linear aliphatic aldehyde. A linear hydrocarbon produced by the method can be used as light oil, and it also can be added to a biofuel.

All publications, patents, and patent applications cited in this specification are intended to be incorporated herein by reference in their entirety.

The invention claimed is:

1. A method for producing a linear hydrocarbon, comprising reacting a linear aliphatic aldehyde in the presence of at least one metal ion selected from the group consisting of a vanadium ion and a thallium ion to produce a linear hydrocarbon.

2. The method according to claim 1, wherein the linear aliphatic aldehyde is a linear aliphatic aldehyde having 8 to 18 carbon atoms.

3. The method according to claim 1, wherein the reaction is carried out in a solvent containing water.

4. The method according to claim 1, wherein the at least one metal ion is a vanadium ion.

5. The method according to claim 3, wherein a concentration of the at least one metal ion in the solvent is 0.1 ppm to 2000 ppm.

6. The method according to claim 3, wherein a concentration of the at least one metal ion in the solvent is 50 ppm to 500 ppm.

7. The method according to claim 3, wherein a concentration of the linear aliphatic aldehyde in the solvent is 0.1 mM to 20 mM.

8. The method according to claim 6, wherein a concentration of the linear aliphatic aldehyde in the solvent is 0.1 mM to 20 mM.

9. The method of claim 3, wherein a ratio of the linear aliphatic aldehyde to the metal ion in the solvent is 1:2 to 1:1000.

10. The method of claim 1, wherein the linear aliphatic aldehyde is selected from the group consisting of octanal, nonanal, decanal, undecanal, dodecanal, tridecanal, tetradecanal, pentadecanal, hexadecanal, heptadecanal, and octadecanal.

* * * * *